United States Patent
Chen et al.

(10) Patent No.: US 8,908,185 B2
(45) Date of Patent: Dec. 9, 2014

(54) COUPLING PRISM AND OPTICAL DETECTION SYSTEM THEREOF

(71) Applicant: National Yang Ming University, Taipei (TW)

(72) Inventors: How-foo Chen, Taipei (TW); Oscar Kuang-Sheng Lee, Taipei (TW)

(73) Assignee: National Yang-Ming University, Taipei (TW)

( * ) Notice: Subject to any disclaimer, the term of this patent is extended or adjusted under 35 U.S.C. 154(b) by 26 days.

(21) Appl. No.: 13/790,408

(22) Filed: Mar. 8, 2013

(65) Prior Publication Data

US 2014/0125979 A1  May 8, 2014

(30) Foreign Application Priority Data

Nov. 2, 2012 (TW) .............................. 101140640 A

(51) Int. Cl.
G01N 21/55 (2014.01)
G02B 5/04 (2006.01)

(52) U.S. Cl.
CPC ................ *G02B 5/04* (2013.01); *G01N 21/553* (2013.01)
USPC ............................ 356/445; 356/369; 356/436

(58) Field of Classification Search
USPC .......................... 356/445–448, 432–440, 369
See application file for complete search history.

(56) References Cited

U.S. PATENT DOCUMENTS

| 6,466,323 B1 * | 10/2002 | Anderson et al. | 356/445 |
| 6,943,897 B1 * | 9/2005 | Stenton et al. | 356/515 |
| 7,728,980 B2 * | 6/2010 | Namiki | 356/445 |
| 2005/0018194 A1 * | 1/2005 | Thirstrup et al. | 356/445 |
| 2013/0342839 A1 * | 12/2013 | Chen | 356/364 |

* cited by examiner

*Primary Examiner* — Hoa Pham
(74) *Attorney, Agent, or Firm* — Muncy, Geissler, Olds & Lowe, P.C.

(57) ABSTRACT

The present invention provides a prism. The prism includes a lower surface, an upper surface, a first side surface and a second side surface. The first side surface and the second side surface are disposed between the upper surface and the lower surface. The first side surface and the second side surface of the prism are one-dimensional parabolic surfaces. The lower surface is used to receive light. The first side surface is used to reflect the light from the lower surface to the upper surface. The second side surface is used to reflect the light from the upper surface to the lower surface for further analysis in the process unit afterwards.

14 Claims, 7 Drawing Sheets

COUPLING PRISM AND OPTICAL DETECTION SYSTEM THEREOF

CROSS-REFERENCE TO RELATED APPLICATIONS

This Non-provisional application claims priority under 35 U.S.C. §119(a) on Patent Application No(s). 101140640 filed in Taiwan, Republic of China Nov. 2, 2012, the entire contents of which are hereby incorporated by reference.

FIELD OF THE INVENTION

This invention relates to a prism, particularly to the prism applied to an optical sensing system.

BACKGROUND OF THE INVENTION

With an optical detection system, an object can be detected to gain detailed analysis information, in which the application of surface plasmon waves is to implement analysis of the object through the Surface Plasmon Waves activated by light. Currently, the application is widely applied to biological detection and its molecular dynamics research including biosensor, immunodiagnosis and dynamic analysis of antibody and antigen. Through the chemical binding specificity of the antigen and its corresponding antibody, surface plasmon resonance is mainly applied to the dynamic analysis of the chemical binding between antibody and antigen in the research of biomedical science. The derivative applications include the detection of the existence of biomolecule, detection of subspecies of certain pathogenic bacteria, and detection and categorization of certain virus, among which the detection of the existence of biomolecule is currently the major derivative application of surface plasmon waves in biomedical science, such as inflammatory biomarker, the detection of cardiovascular disease using C-reactive protein, the detection of subspecies of certain pathogenic bacteria, and detection and categorization of certain virus.

The basic framework of a surface plasmon wave sensor is a sensing device that detects a change of the resonance condition between an incident light beam and surface plasmon wave on the interface of metal and dielectrics, and the change of the resonance is caused by the refractive index change of the dielectrics, which can be a result of antigen capture or molecular binding, molecular folding, deformation, or any other changes of the tested material close to or on the interface.

The change can be gained from measuring the optical property of the reflected light of laser beam. Regarding the measurement on different optical properties of the reflected light beam, the measuring modes can be classified as angle, amplitude, wavelength, and phase mode. As for the operation procedure, though the measuring modes of amplitude and phase are static, the light path of the incident light beam needs to be adjusted before implementing measurement to receive the maximum sensitivity: the incident angle of the beam to obtain the largest change in amplitude with the refractive index change of dielectric substance, or the resonance angle for phase mode has to be located. When the system design does not allow incident angle adjustment, the detectable range of refractive index and sensitivity will be much restricted. Only when the system is operated under wavelength mode, a satisfied measuring dynamic range can be gained without changing the incident angle, except that the sensitivity is not as good as phase mode measurement. Moreover, the angle measuring mode is inherently dynamic, the incident angle of the light beam needs to be scanned repetitively during the measurement.

Traditional surface plasmon resonance instruments implementing corresponding rotation using two-arm rotating stage, in order to achieve the capability of adjusting the incident angle of the light beam. However, there are several disadvantages:

a. The incident light source and the receiving terminal are not fixed, which will limit the size, weight, and complexity of the light source system and the optical detection system. This also means that a detection method of a phase mode and an amplitude mode will be restricted.

b. The resolution, accuracy, and stability, of a rotation stage are not as good as a linear motorized stage. Besides, two rotation stages are not cost effective compared to a linear stage.

c. Due to the structural limitation of optical elements, the coupling side of the coupling prism is mainly oriented vertically. When matching oil is used to couple a glass slide and the prism, the matching oil is easy to evaporate after a long time use. As a result, the system stability and measurement consistency in the long time use are not easy to maintain.

d. The vertical orientation of the prism coupling face is not suitable for the design and operation of a micro-fluidics chip.

e. The vertical orientation of prism coupling face cannot be incorporated into an image system, particularly a microscopy system, because the design of vertical light path for image capture is mainly adopted in microscopy system.

There is another way to adjust the incident angle of the light beam by incorporating a galvo mirror scanning system. In this method, the light path of the reflected beam will be deflected from the designed incident angle of the optical elements and detectors in the detection system. This beam deflection caused by incident angle tuning will result in the impossibility of implementing phase detection. However, phase detection usually has higher sensitivity.

In the last few years, although the models of all kinds of detection modes have different advantages, there is still a lack of the design that can integrate several modes into one device. With current devices, operation modes (resonance angle mode and amplitude measuring mode) with a large dynamic range usually cannot meet the requirement of high sensitivity, and the incident angle of the light beam in a device performing a phase mode is usually fixed; therefore, its dynamic range is extremely small.

U.S. Pat. No. 7,265,844 discloses a horizontal surface plasmon resonance instrument that is claimed to be able to adjust incident angle through a complicated mechanical motion and track with special curves, and thus fix the position of the light source and the optical detection unit. However, the accuracy and stability are not satisfying.

Moreover, FIG. 1 is also a prior art, which is the illustration of surface Plasmon wave detection system disclosed by the inventor of the present invention. As illustrated, the surface Plasmon system 100 includes a light source unit 110, a control unit 120, a detection unit 130 and a process unit 140.

The light source unit 110 includes: a semiconductor laser 111, a polarizing beam splitter 112 and a half-wave plate 113, used to direct the light into the control unit 120.

The control unit 120 includes: a motorized stage 121, a right angled triangle mirror 122, two-dimensional parabolic mirror 123a and 123b and a hemispherical lens 124. The light is directed by the triangle mirror 122 into the two-dimensional parabolic mirror 123a. The two-dimensional parabolic mirror 123a first directs the light into the hemisphere lens

124, and the hemisphere lens 124 then directs the light into the two-dimensional parabolic mirror 123b. At last, the light is directed into the triangle mirror 122 through the two-dimensional parabolic mirror 123b and output to the detection unit 130.

The detection unit 130 includes: a non-polarizing beam splitter 131, a polarizing beam splitter 132, a detection element 133, an amplifier 134, a wave plate 135 and a control element 125. Through the optical property detected by the detection unit 130, the signal is sent to the process unit 140 for further analysis.

Users, through the adjustments of motorized stage 121 and the two-dimensional parabolic mirror 123a and 123b, can detect the object to maintain the incident angle of the laser beam at the largest angle that causes the largest change in refraction index in amplitude, or the best resonance angle for energy coupling to detect the changes caused by the refractive index of the medium.

However, hemisphere lens and the two-dimensional mirror will both cause the complexity in light path adjustment and beam path deflection after long time operation. Slight deflection in the light path of the incident light will cause an error in the incident angle and the enlargement of deflection in the light path. This shortage will cause difficulty in the detection of the optical phase and the resonance angle for the receiving terminal, which might cause a detection error or, in the worst scenario, a situation of not being able to implement the detection. Moreover, the system needs to be used with two two-dimensional off-axis parabolic mirror 123a and 123b at the same time. This will cause much more difficulty in the adjustment of positions of the three optical components. Therefore, users cannot easily scan the full incident angle without changing the light path to the detection unit 130. When the implementation of the angle scanning with a large range without the occurrence of light path deflection is desired, it will take a long time to adjust the relative positions of the coupling prism and two off-axis parabolic mirrors as well as the path incident light. Moreover, due to the focusing effect of the hemisphere lens 124 and the two-dimensional parabolic mirror 123a and 123b, the activation spot of the incident light will be very small which can only be used for the detection of single spot or single channel. Moreover, this design is not equipped with a mirror that directs horizontal propagation light into vertical propagation, so it's not easy to be integrated into a microscopy system.

SUMMARY OF THE INVENTION

The prism of the invention includes a lower surface, an upper surface, a first side surface and a second side surface. Wherein, the first side surface and the second side surface of the prism are one-dimensional parabolic surfaces.

The lower surface is used to receive light. The upper surface is opposite to the lower surface. The first side surface is used to reflect the light from the lower surface to the upper surface. The second side surface is used to reflect the light from the upper surface to the lower surface. Wherein, the first side surface and the second side surface are disposed between the upper surface and the lower surface.

Preferably, the light is respectively reflected through internal angles of reflection of the first side surface and the second side surface. The angle formed by the light being reflected from the first side surface to the upper surface is larger than the critical angle of the total internal reflection. The angle formed by the light being reflected from the upper surface to the second side surface is also larger than the critical angle of the total internal reflection. All the reflection occurred in the prism are total internal reflection. Therefore, no mirror coating is required.

The optical detection system is also provided in the present invention. The optical detection system includes a light source unit, a control unit and a detection unit.

The light source unit is used to provide a light source. The control unit includes a prism. The prism includes a lower surface, an upper surface, a first side surface and a second side surface. Wherein, the first side surface and the second side surface are disposed between the upper surface and the lower surface, and the first side surface and the second side surface of the prism are one-dimensional parabolic surfaces.

After the light enters the control unit, the light is directed into the lower surface of the prism. The lower surface reflects the light to the first side surface of the prism. After that, the first side surface reflects the light to the upper surface of the prism. Then, the upper surface directs the light to the second side surface. Likewise, the second side surface directs the light to the lower surface of the prism. At last, the light is outputted to the detection unit.

The detection unit is used to detect the light coming from the control unit to output a signal.

Preferably, the control unit further includes a triangle mirror. The triangle mirror includes a first reflection side and a second reflection side. The first reflection side is used to receive the light from the light source unit and direct the light into the prism. The second reflection side is used to receive the light from the prism and direct the light into the detection unit.

Preferably, the control unit further includes a first stage motion controller and a second stage motion controller. The first stage motion controller is connected to the triangle mirror, and the second stage motion controller is connected to the prism.

Preferably, the optical detection system further includes a process unit used to receive the signals for analysis afterwards.

Users control the incident angle of the light entering the cylindrical lens through the first stage motion controller, and implement multiple spots scanning with fixed incident light through the second stage motion controller, so as to detect the object and maintain the incidence angle of the light into the cylindrical lens at the largest angle that causes the largest change in amplitude or the best resonance angle for energy coupling to detect the changes caused by the refractive index of the medium.

The fixation of the light source unit and the detection unit of the present invention, accompanied with the properties that the incidence angle of the light can be adjusted and scanned, make it possible to implement surface plasmon wave measuring modes, such as resonance angle, amplitude, wavelength, phase, etc at the same time. The present invention has both the properties of a large dynamic range and high sensitivity; moreover, it is easy to adjust the light path. Also, the present invention can be easily integrated into a microscopy system, which makes the invention very practical.

The optical detection system of the invention can make the light path easy to be adjusted because of using the three total reflection planes to reflect light. The three total reflection planes are respectively the first side surface, the upper surface where the focus line lies on, and the second side surface. Light in a single prism can decrease the adjustment procedure and can miniaturize the system. It even doesn't need refractive index matching oil, so it can be used for a long time and have the advantage of low cost and can be disposable.

The advantages and spirit of the present invention, and further embodiments can be further understood with the following embodiments and appended figures.

DETAILED DESCRIPTION OF THE INVENTION

For clarity of disclosure, and not by way of limitation, the detailed description of the invention is divided into the subsections that follow.

To further illustrate the present invention, the following specific examples are provided.

Figure 1:
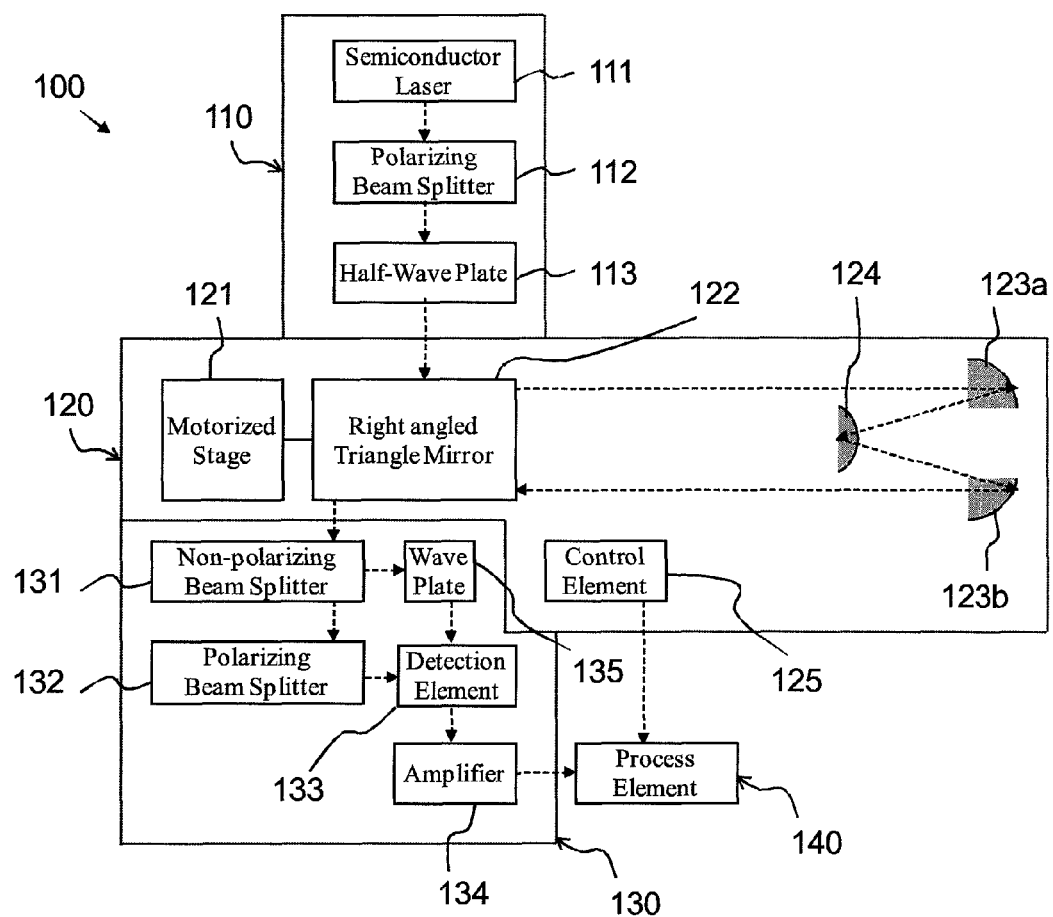
FIG. 1 illustrates the surface plasmon wave detection system of prior art.
Figure 2A:
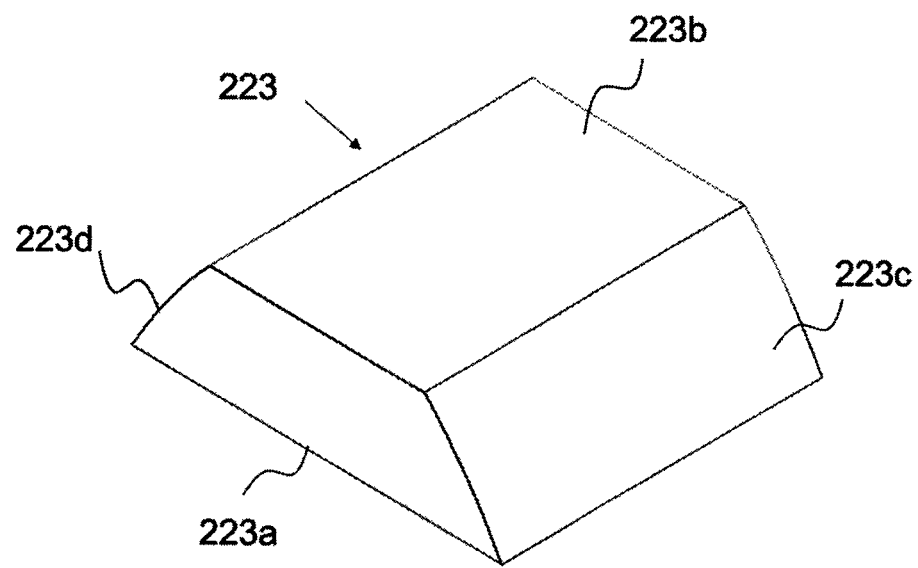
FIG. 2(a) is a diagram to show the shape of the prism in the invention.
Figure 2B:
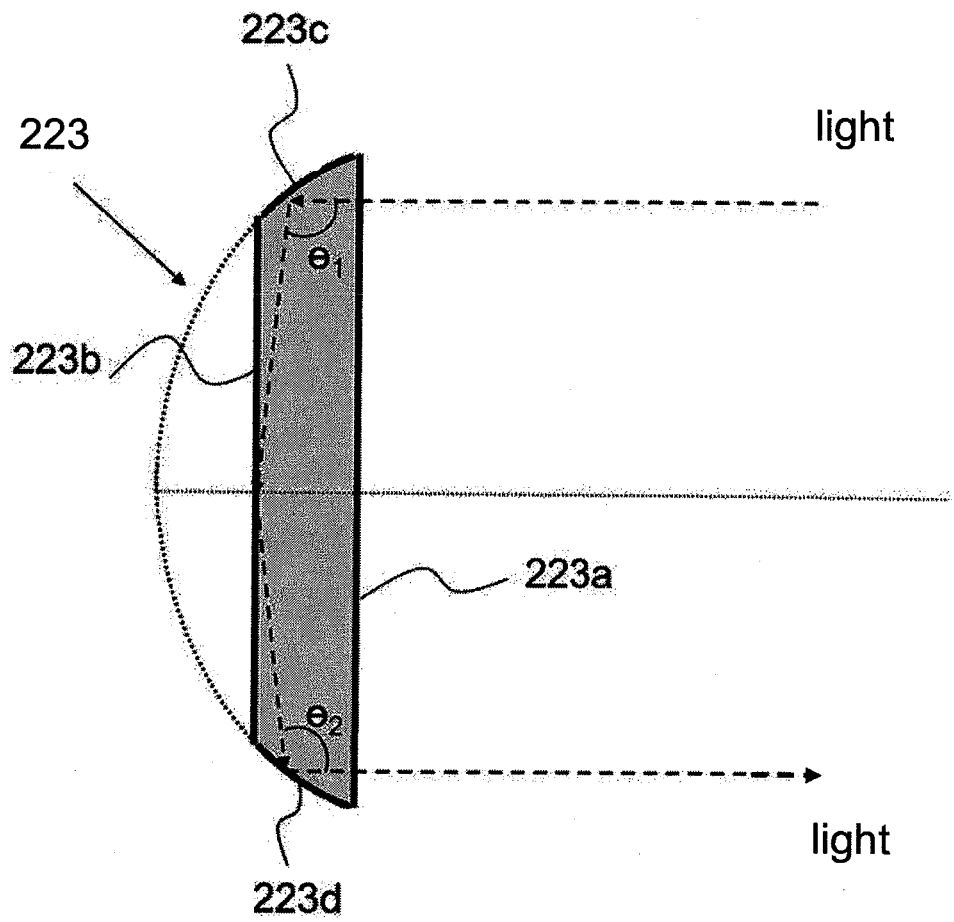
FIG. 2(b) is a diagram to show the light path of the prism in the invention.

Please refer to FIG. 2(a) and FIG. 2(b). FIG. 2(a) is a diagram to show the shape of the prism in the invention. FIG. 2(b) is a diagram to show the light path of the prism in the invention. The prism 223 of the invention includes a lower surface 223a, an upper surface 223b, a first side surface 223c and a second side surface 223d.

The lower surface 223a is used to receive light. The upper surface 223b is opposite to the lower surface 223a. The first side surface 223c is used to reflect the light from the lower surface 223a to the upper surface 223b. The second side surface 223d is used to reflect the light from the upper surface 223b to the lower surface 223a. Wherein, the first side surface 223c and the second side surface 223d are disposed between the upper surface 223b and the lower surface 223a.

The first side surface 223c and the second side surface 223d of the prism 223 are one-dimensional parabolic surfaces, so the light can be directed to a focus line by the parabolic surface. The focus line is in general on the upper plane surface 223B. But when microfluidics built on a substrate slide is attached on the prism, the focus line of the parabolic curve is then on the upper surface of the substrate slide. The prism then should be peeled off by the thickness of the substrate slide. Matching oil is then applied between the substrate and the prism to make them as one piece optically. In the invention, the light is respectively reflected through internal angles of reflection of the first side surface 223c and the second side surface 223d. The angle $\theta_1$ formed by the light being reflected from the first side surface 223c to the upper surface 223b is larger than the critical angle of the total internal reflection. The angle $\theta_2$ formed by the light being reflected from the upper surface 223b to the second side surface 223d is larger than the critical angle of the total internal reflection. All the reflection occurred in the prism are total internal reflection. Therefore, no mirror coating is required, but not limited herein.

The incident light emitted into the prism 223 is from the lower surface 223a. The incident light and the emergent light in the prism 223 are parallel to the optical axis, but not limited herein.

In an embodiment, the lower surface 223a of the prism 223 can be parallel to the upper surface 223b. The lower surface 223a of the prism 223 can be also not parallel to the upper surface 223b, and not limited herein.

Figure 2C:
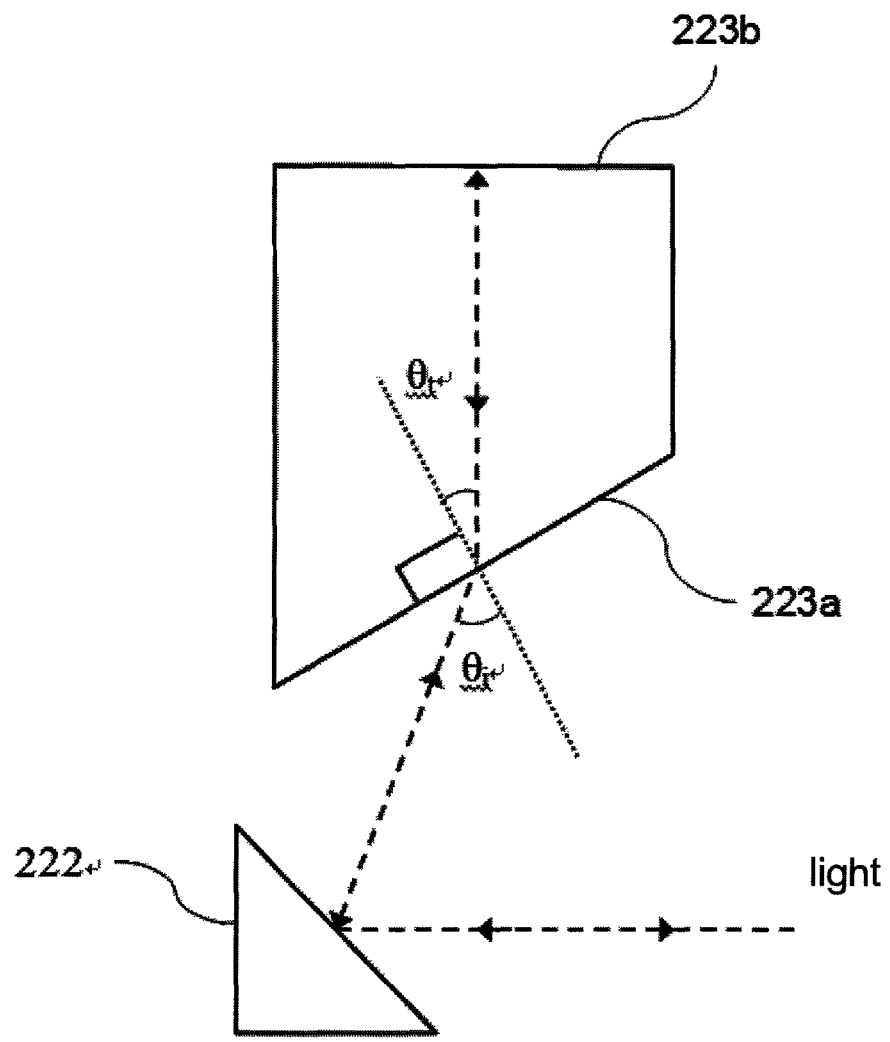
FIG. 2(c) is a lateral view to show the light path of the prism in the invention.

Please refer to FIG. 2(c). FIG. 2(c) is a lateral view to show the light path of the prism in the invention. In the embodiment, the lower surface 223a is not parallel to the upper surface 223b, the incident angle $\theta_i$ to the lower surface 223a and the angle of refraction $\theta_r$ are not limited, but the light path of the prism 223 is parallel to the plane of incidence of the upper surface 223b. When the lower surface 223a is not parallel to the upper surface 223b, it not only can avoid the main light path occurring multiple reflection interference, but also can avoid the non-perpendicular light incidence causing the detection point from drift in the situation that the angle varies, but not limited herein.

In an embodiment, the prism 223 can be made of optical resin by injection molding production, but not limited herein.

Figure 3:
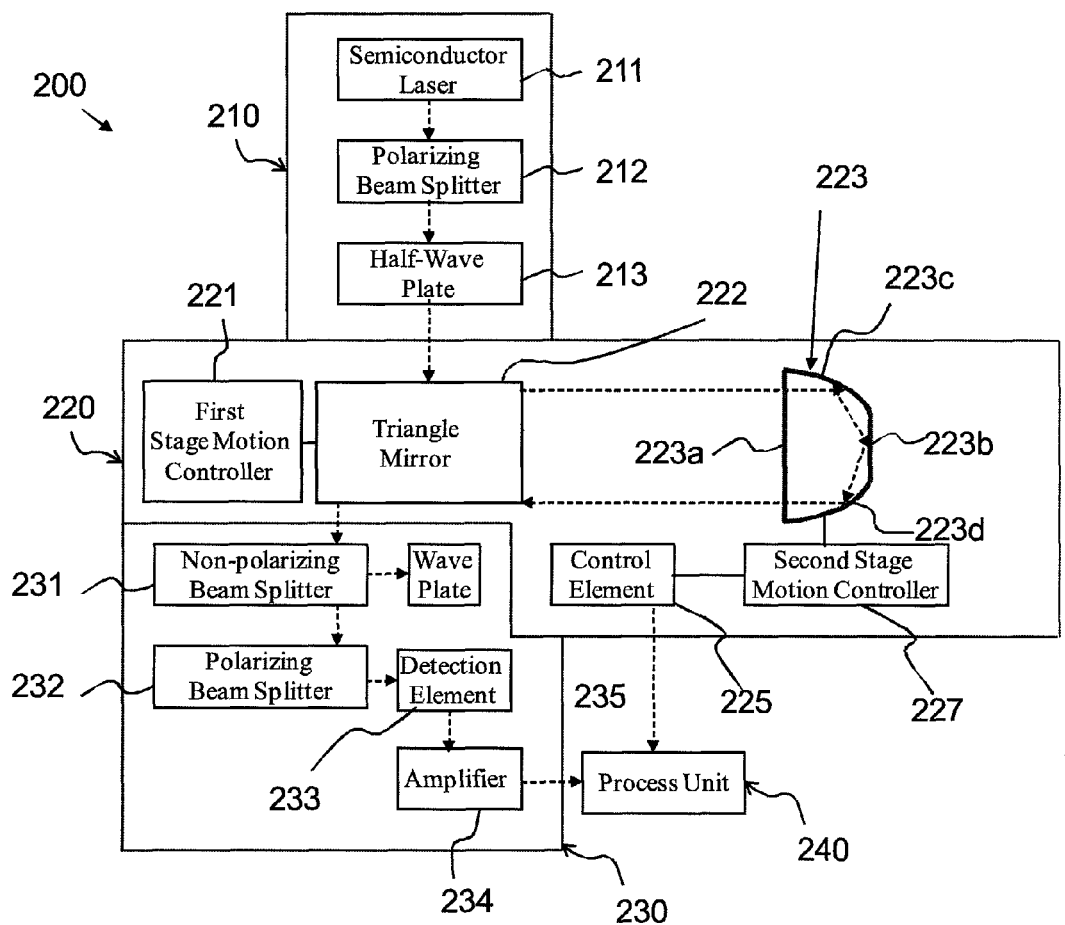
FIG. 3 is a diagram to show the optical detection system in the invention.
Figure 4:
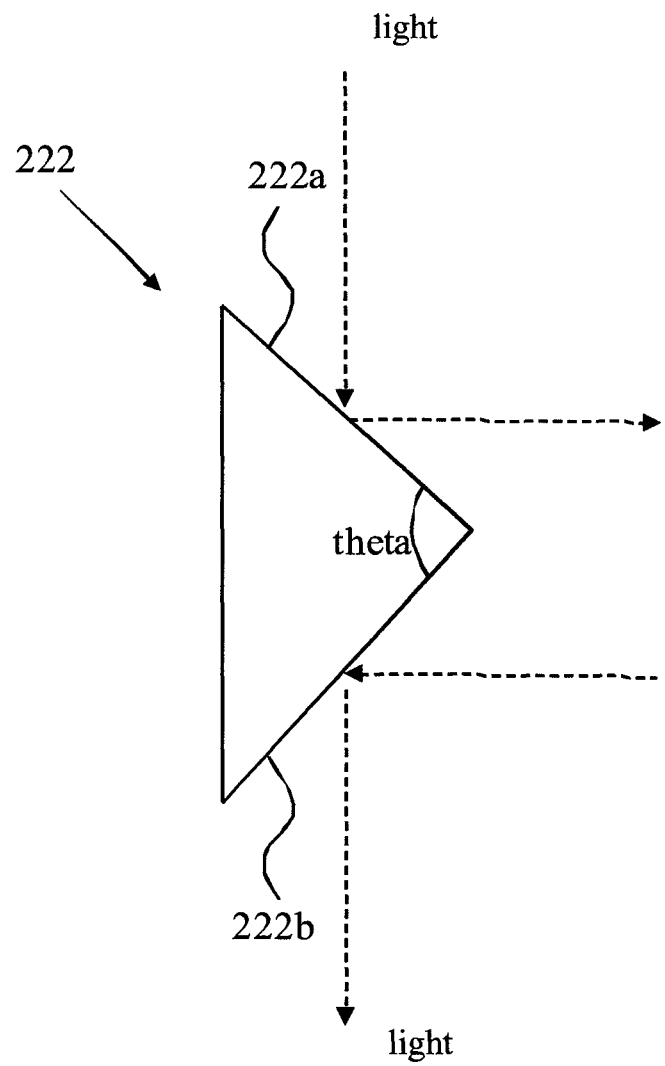
FIG. 4 is a diagram to show the triangle mirror of the optical detection system in the invention.

Please refer to FIG. 3 and FIG. 4. FIG. 3 is a diagram to show the optical detection system in the invention. FIG. 4 is a diagram to show the triangle mirror of the optical detection system in the invention. The optical detection system 200 of the present invention includes a light source unit 210, a control unit 220, a detection unit 230 and a process unit 240.

The light source unit 210 contains a semiconductor laser 211, a polarizing beam splitter 212 and a half-wave plate 213. The semiconductor laser 211 is used to provide a light source, and the light is directed into the control unit 220 through polarizing beam splitter 212 and the half-wave plate 213. The semiconductor laser 211 can also be replaced by an LED or other light source, but not limited herein.

The control unit 220 includes a first stage motion controller 221, a triangle mirror 222, a prism 223, a control element 225 and a second stage motion controller 227, wherein the triangle mirror 222 includes a first reflection side 222a and a second reflection side 222b.

After the light enters the control unit 220, the horizontal propagation light is directed into the lower surface 223a of the prism 223 through the first reflection side 222a of the triangle mirror 222. The lower surface 223a reflects the horizontal propagation light to the first side surface 223c of the prism 223. After that, the first side surface 223c reflects the light to the upper surface 223b of the prism 223. Then, the upper surface 223b directs the light to the second side surface 223d. Likewise, the second side surface 223d directs the light to the lower surface 223a of the prism 223. At last, the light is converted back to the second reflection side 222b of the triangle mirror 222. Then the light is outputted to the detection unit 230 by the second reflection side 222b of the triangle mirror 222.

In the embodiment above, the angle (denoted as theta) of the two mirrors of the triangle mirror 222 is not limited to a right angle (90 degrees), and the equation of the displacement of the mirror ($L_M$) and that of incident light beam ($L_B$) is $L_B = L_M * \sin(\text{theta})$. When the theta between the two reflection sides of the triangle mirror 222 is not 90 degrees, sin(theta) is the enhancing factor of light displacement resolution. When the theta is 90 degrees, the light reflected by the second reflection side 222b will coincide with the incident light of the first reflection side 222a.

In one embodiment, the triangle mirror 222 can be replaced by a mirror of polarizing or non-polarizing beam splitter, which is not limited with the illustrated invention. In one embodiment, the triangle mirror 222 can be a mirror, not limited with the illustrated invention.

In one embodiment, the first stage motion controller 221 is connected to a motorized translation stage (not illustrated) where the triangle mirror 222 is located to provide the power and signal needed for moving the reflection position of the light on the triangle mirror 222. By the movement of the motorized translation stage, the incident angle of the light that goes in the prism 223 can be changed.

In one embodiment, the second stage motion controller 227 is connected a motorized translation stage (not illustrated) where the prism 223 is located to provide the power and signal needed for moving the reflection position of the light on the first side surface 223c and the second side surface 223d. By the movement of the motorized translation stage, the light can be guided to implement linear scanning with fixed incidence angle on the plane part of the upper surface 223b. The scanning angle is according to the distance of the incidence light toward the light axis, and the scanning range is according to the size of the prism 223.

Figure 5A:
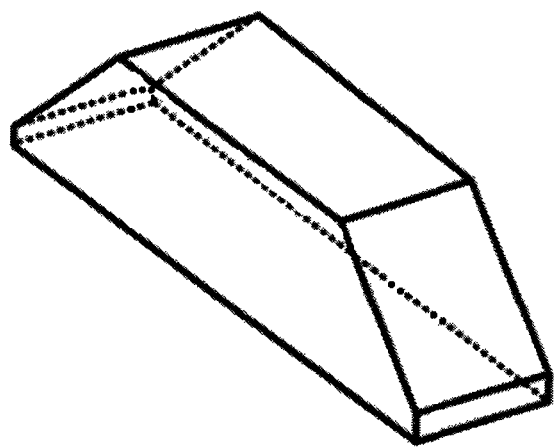
FIG. 5(a) is a diagram to show the shape of a Dove prism.
Figure 5B:
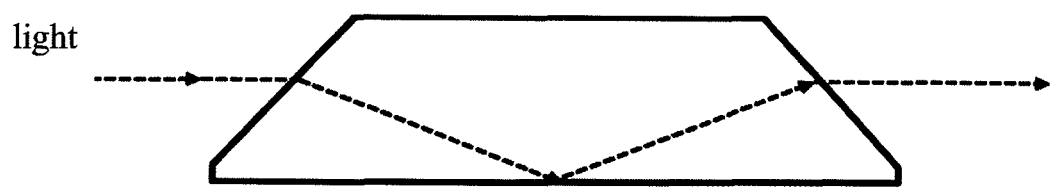
FIG. 5(b) is a diagram to show the light path of the Dove prism.

The prism of the invention is different from a Dove prism. FIG. 5(a) is a diagram to show the shape of the Dove prism. FIG. 5(b) is a diagram to show the light path of the Dove prism. The Dove prism uses the principle of light refraction that the excitation light is refracted to the lower surface to generate an evanescent wave. When arriving at the Dove prism, the excitation light occurs partially reflection and partially refraction, but not all of the light energy are used to excite a surface plasmon wave. The prism of the invention uses the principle of total reflection of light that total light energy can be used to excite the surface plasmon wave. The Dove prism is only used for a fixed incident angle, and unable to achieve the effect of scanning incident angle as the prism used in the invention.

In one embodiment, the light source provided by light source unit 210 is a spot. When the optical detection system 200 of the present invention is applied to surface plasmon wave biomedical detection element, multiple spots detection can be implemented. In another embodiment, if the light provided by the light source unit 210 is a linear light source, the optical detection system 200 of the present invention can implement multiple channels or linear multiple spots simultaneous detection.

The control unit 225 is electrically connected to the first stage motion controller 221 and the second stage motion controller 227 to control the movement and the position of the motorized translation stages.

The detection unit 230 includes a non-polarizing beam splitter 231, a polarizing beam splitter 232, at least a detection element 233, an amplifier 234 and a wave plate 235. The detection unit 230 detects the light property and generates a signal, and then transmits the signal to the process unit 240 for further analysis. In one embodiment, the detection element 233 can be a photodiode, a CCD image sensor or a CMOS image sensor and the wave plate 235 can be ¼ wave plate, but not limited herein.

The process unit 240 is used to receive the signals for further analysis. Meanwhile, the control element 225 of the control unit 220 is also electrically connected to the process unit 240. Since the process unit 240 can transmit signals and can control the control element 225, the process unit 240 can process the signals received from the detection unit 230 and the control unit 220. In one embodiment, the process unit 240 can be a computer, but not limited herein.

The optical detection system of the invention can make the light path easy to be adjusted because of using the three total reflection planes to reflect light. The three total reflection planes are respectively the first side surface 223c, the second side surface 223d and the plane through the focus, the upper surface 223b. Light in a single prism 223 can decrease the adjustment procedure and can miniaturize the system. It even doesn't need refractive index matching oil, so it can be used for a long time and have the advantage of low cost and can be disposable.

In addition, users can detect the object and make the incident angle of the light that goes onto the upper surface 223b at the fixed angle that causes the largest change in amplitude, or the best resonance angle for energy coupling to detect the changes caused by the refractive index of the medium by using the first stage motion controller 221, the second stage motion controller 227, accompanied with the adjustment of the prism 223. Due to the first side surface 223c and the second side surface 223d are parabolic surface and they are both one-dimensional, the light path is simple. As a result, the adjustment of the incidence angle of light can be achieved under the circumstance that both the light source unit and the detection unit are fixed (i.e. the positions of transmitting and receiving light are fixed). Moreover, the light path is easy to adjust, so it's very practical.

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

What is claimed is:

1. A prism, comprising:
    a lower surface, used to receive light;
    an upper surface, opposite to the lower surface;
    a first side surface, a one-dimensional parabolic surface, used to reflect the light from the lower surface to the upper surface; and
    a second side surface, a one-dimensional parabolic surface, used to reflect the light from the upper surface to the lower surface;
    wherein, the first side surface and the second side surface are disposed between the upper surface and the lower surface,
    wherein the light is respectively reflected in the prism from the lower surface to the upper surface and vice versa by the first side surface and the second side surface,
    wherein the incident angle of the light impinging onto the first side surface and then reflected to the upper surface is larger than the critical angle of the total internal reflection, and
    wherein the incident angle of the light, from the upper surface, impinging onto the second side surface is larger than the critical angle of the total internal reflection.

2. The prism according to claim 1, wherein the lower surface of the prism is parallel to the upper surface.

3. The prism according to claim 1, wherein the lower surface of the prism is not parallel to the upper surface.

4. An optical detection system, comprising:
    a light source unit, used to provide light;
    a prism, comprising:
        a lower surface, used to receive the light;
        an upper surface, opposite to the lower surface;
        a first side surface, a one-dimensional parabolic surface, used to reflect the light from the lower surface to the upper surface; and
        a second side surface, a one-dimensional parabolic surface, used to reflect the light from the upper surface to the lower surface;

wherein, the first side surface and the second side surface are disposed between the upper surface and the lower surface, wherein the light is respectively reflected in the prism from the lower surface to the upper surface and vice versa by the first side surface and the second side surface, wherein the incident angle of the light impinging onto the first side surface and reflected to the upper surface is larger than the critical angle of the total internal reflection, and wherein the incident angle of the light, from the upper surface, impinging onto the second side surface is larger than the critical angle of the total internal reflection; and a detection unit, detecting the light coming from the control unit to output a signal.

5. The optical detection system according to claim 4, wherein the control unit further comprises a triangle mirror, having a first reflection side and a second reflection side, in which the first reflection side is used to receive light from the light source unit and direct the light into the lower surface of the prism; the second reflection side is used to receive light from the lower surface and direct the light into the detection unit.

6. The optical detection system according to claim 5, wherein the control unit further comprises a first stage motion controller connected to the triangle mirror.

7. The optical detection system according to claim 6, wherein the triangle mirror is located at a motorized translation stage.

8. The optical detection system according to claim 6, wherein the control unit further comprises a second stage motion controller connected to the prism.

9. The optical detection system according to claim 8, wherein the prism is located at a motorized translation stage.

10. The optical detection system according to claim 8, wherein the control unit further comprises a control element electrically connected to the first stage motion controller and the second stage motion controller.

11. The optical detection system according to claim 4, wherein the detection unit comprises a non-polarizing beam splitter, a polarizing beam splitter, an amplifier, a wave plate and at least a detection element.

12. The optical detection system according to claim 11, wherein the detection element is a photodiode, a CCD image sensor or a CMOS image sensor.

13. The optical detection system according to claim 4, wherein further comprises a process unit to receive and process signals.

14. The optical detection system according to claim 4, wherein when a microfluidic substrate slide is attached on the prism, the prism then should be peeled off by the thickness of the microfluidic substrate slide.

* * * * *